United States Patent
Maekawa et al.

(10) Patent No.: US 6,490,824 B1
(45) Date of Patent: Dec. 10, 2002

(54) METHOD FOR CULTURING A BASIDIOMYCETOUS FUNGUS IN A LIQUID CULTURE MEDIUM

(75) Inventors: Takaaki Maekawa, Ibaraki (JP); Keo Intabon, Tsukuba (JP)

(73) Assignee: Tsukuba Biosystems, Ltd., Ibaraki (JP)

( * ) Notice: Subject to any disclaimer, the term of this patent is extended or adjusted under 35 U.S.C. 154(b) by 0 days.

(21) Appl. No.: 09/958,664

(22) PCT Filed: Apr. 20, 2000

(86) PCT No.: PCT/JP00/02595

§ 371 (c)(1),
(2), (4) Date: Oct. 12, 2001

(87) PCT Pub. No.: WO00/65029

PCT Pub. Date: Nov. 2, 2000

(30) Foreign Application Priority Data

Apr. 23, 1999 (JP) .......................................... 11-116188

(51) Int. Cl.[7] .................................................. A01G 1/04
(52) U.S. Cl. ............................................. 47/1.1; 47/1.4
(58) Field of Search ...................................... 47/1.1, 1.4

(56) References Cited

U.S. PATENT DOCUMENTS

| | | | |
|---|---|---|---|
| 2,693,665 A | 11/1954 | Humfeld | |
| 2,761,246 A | 9/1956 | Szuecs | |
| 2,850,841 A | 9/1958 | Szuecs | |
| 3,828,470 A | * 8/1974 | Stoller | 47/1.4 |
| 4,071,973 A | * 2/1978 | Izuka et al. | 47/1.1 |
| 4,127,965 A | * 12/1978 | Mee | 47/1.1 |
| 4,420,319 A | * 12/1983 | Holtz | 71/5 |
| 4,873,195 A | * 10/1989 | Kubo et al. | 435/254 |
| 5,186,731 A | * 2/1993 | Parker | 71/5 |
| 5,888,803 A | * 3/1999 | Starkey | 435/254.1 |
| 5,934,012 A | * 8/1999 | Holtz et al. | 47/1.1 |

FOREIGN PATENT DOCUMENTS

| GB | 2108151 | 5/1983 |
|---|---|---|
| JP | 60-54324 | 3/1985 |

* cited by examiner

*Primary Examiner*—Charles T. Jordan
*Assistant Examiner*—Bret Hayes
(74) *Attorney, Agent, or Firm*—Wenderoth, Lind & Ponack, L.L.P.

(57) ABSTRACT

Disclosed is an efficient method for culturing an edible basidiomycetous fungus such as Mushroom Agaricus Blazei Murill in a liquid culture medium to give fungus aggregates of several centimeter size. Characteristically, the liquid culture medium is formulated with sucrose as a carbon source in the form of crude cane sugar in combination with a water-insoluble growth-supporting material in the form of a fine powder to serve as the core of the fungus aggregates as selected from crushed sugarcane, sugarcane bagasse, pine trees and wheat bran. Further characteristically, the culturing procedure is carried out under an oxygen-enriched condition by blowing oxygen-enriched air of at least 30% by volume oxygen into the culture medium under pressurization at 0.12 to 0.5 MPa (absolute) in a specified blowing rate.

6 Claims, 6 Drawing Sheets

METHOD FOR CULTURING A BASIDIOMYCETOUS FUNGUS IN A LIQUID CULTURE MEDIUM

TECHNICAL FIELD

The present invention relates to a novel and efficient method for culturing a basidiomycetous fungus in an aqueous liquid culture medium or, more particularly, to a method for culturing an edible basidiomycetous fungus such as Mushroom Agaricus Blazei Murill, Cortinellus shuitake, Lyophyllum aggregatum, Pleurotus ostreatus and the like in an aqueous liquid culture medium to obtain aggregates of the fungus body having a several centimeter size as well as to a bioreactor for practicing the culturing method.

BACKGROUND ART

Methods for culturing a basidiomycetous fungus in a liquid culture medium are known as disclosed, for example, in U.S. Pat. Nos. 2,693,665, 2,761,246 and 2,850,841 and elsewhere. A typical liquid culture medium used in the prior art contains 50 g of sucrose, 10 g of ammonium nitrate, 5 g of sodium phosphate, 2.5 g of magnesium sulfate and 0.2 g of iron (II) sulfate each per liter of the liquid culture medium. The liquid culture medium inoculated with the fungus body such as mycelia is gently agitated with a stirrer rotating at a relatively low revolution in air for several days to effect growth of the mycelia into aggregates of globular or polyhedral granules having a diameter of 3 to 40 mm. It is accepted that such an aggregate of mycelia is formed by virtue of the viscous polysaccharide material formed on the surface of the mycelium to act like an adhesive. The productivity of these prior art methods, however, is very low due to the low growth rate of the fungus and a difficulty encountered in the recovery of the fungus body as grown from the culture medium.

The present invention accordingly has an object to provide a novel and efficient industrial method for culturing a basidiomycetous fungus such as Mushroom Agaricus Blazei Murill, referred to as Agaricus fungus hereinafter, and the like in a liquid culture medium. A secondary object of the invention is to provide a novel bioreactor suitable for practicing the above mentioned culturing method in a liquid culture medium for the fungus.

DISCLOSURE OF INVENTION

Thus, the method of the present invention for culturing a basidiomycetous fungus in an aqueous liquid culture medium comprises the steps of:

(a) inoculating a liquid culture medium containing inorganic nutrient salts for nitrogen, phosphate and potassium with a body of the fungus such as mycelia;
(b) admixing the liquid culture medium with crude cane sugar in an amount in the range from 50 g to 70 g calculated as sucrose per liter of the liquid culture medium;
(c) admixing the liquid culture medium with a water-insoluble growth-supporting material selected from the group consisting of crushed sugarcane, sugarcane bagasse and wheat bran in an amount in the range from 0.2 g to 15 g as dry per liter of the liquid culture medium;
(d) keeping the liquid culture medium under agitation at a temperature in the range from 20 to 30 ° C.; and
(e) blowing, into the liquid culture medium, oxygen-enriched air containing at least 30% by volume or, preferably, from 60 to 90% by volume of oxygen under a pressure in the range from 0.12 to 0.5 MPa (absolute) at a rate of at least 0.01 liter/minute per liter of the liquid culture medium.

The bioreactor for practicing the above described inventive culturing method comprises:

(A) a pressurizable vessel for containing a liquid culture medium;
(B) a gas inlet tube capable of blowing oxygen-enriched air into the liquid culture medium under a superatmospheric pressure in the range from 0.12 to 0.5 MPa (absolute);
(C) gas outlet tube having a means for regulating the pressure inside of the pressurizable vessel at a pressure in the range from 0.12 to 0.5 MPa (absolute); and
(D) a means for agitating the liquid culture medium contained in the pressurizable vessel.

BEST MODE FOR CARRYING OUT THE INVENTION

Figure 1:
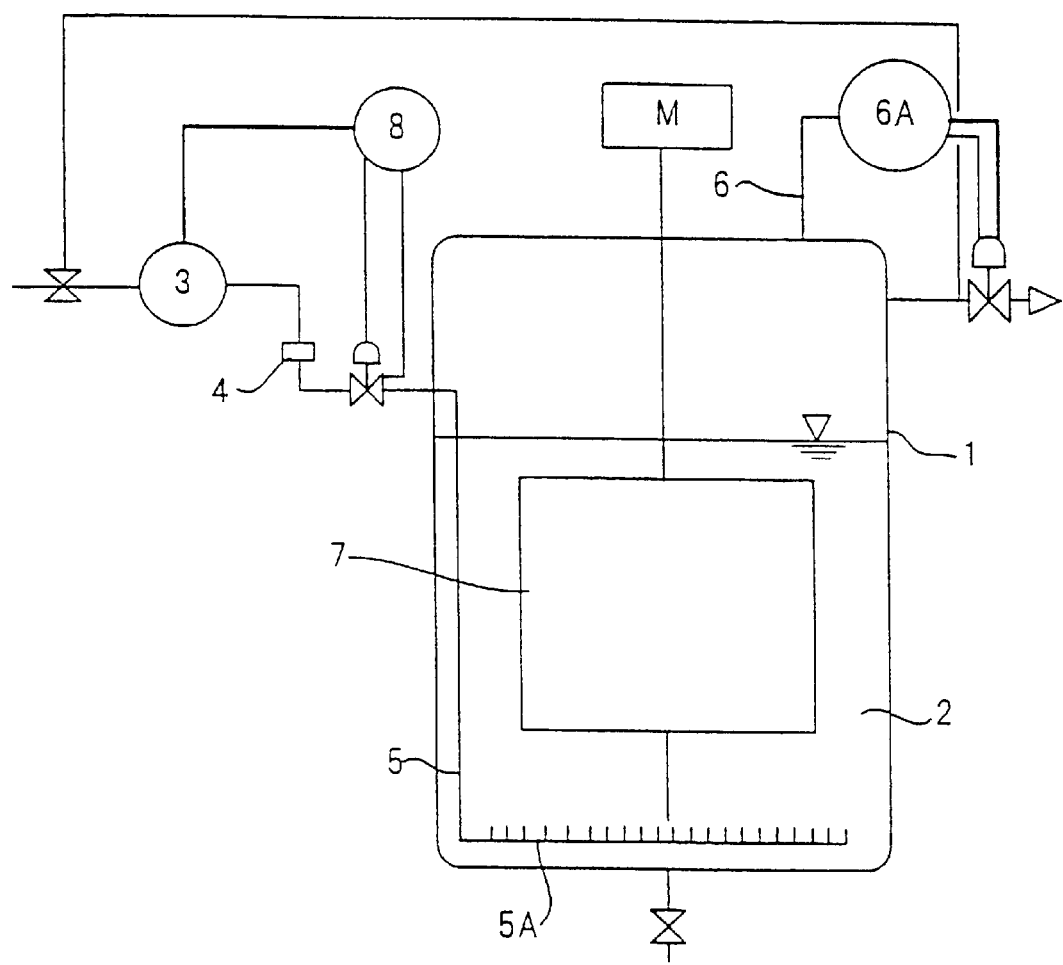
FIG. 1 is a schematic cross sectional view of a typical bioreactor system for practicing the method of the invention.

As is described above, the inventive method for culturing a basidiomycetous fungus or, typically, the Agaricus fungus is characterized in both of the constituents in the liquid culture medium and the running conditions of the culturing process in such a liquid culture medium. When the culturing process is conducted under most desirable conditions, the aggregates of the fungus body granules show rapid growth to give an aggregate having a diameter of 10 to 20 mm if the nutrients are sufficiently provided in the culture medium although the core portion of the aggregates sometimes exhibits a dark color presumably as a consequence of local deficiency in the dissolved oxygen in the liquid culture medium. This problem can be solved by increasing the concentration of the dissolved oxygen in the culture medium up to 15 to 30 mg/liter so that the aggregates of the fungus body granules can be grown to have an approximately 40 mm diameter without blackening in the core portion by a culturing run continued for 3 to 4 days.

The kinds and concentration of inorganic nutrient salts are not particularly limitative but can be conventional including 10 to 15 g/liter of ammonium nitrate as a nitrogen source, 5 to 7 g/liter of sodium phosphate as a phosphate source, 3 to 7 g/liter of potassium sulfate or dipotassium hydrogenphosphate as a potassium source, 2.5 to 3.5 g/liter of magnesium sulfate and 0.2 to 0.3 g/liter of iron(II) sulfate.

Characteristically, the liquid culture medium used in the inventive culturing method is admixed with sucrose as a carbon source which is not in the form of a purified sugar but in the form of a crude cane sugar. The initial amount of the crude cane sugar in the liquid culture medium is in the range from 40 to 200 g/liter calculated as pure sucrose. It is essential that the sucrose is added to the medium as a crude cane sugar and not as a crude beat sugar. Although the reason for this limitation to crude cane sugar is not well understood, it is presumable that, while crude sugars, which may be from sugarcanes or from beats, always contain a substantial amount of impurities besides sucrose, the kinds of the crude sugar impurities are different between crude cane sugar and crude beat sugar and the impurities contained in the crude cane sugar including certain metallic elements such as manganese, zinc and cobalt as well as other unidentified trace elements are particularly effective for promoting growth of the Agaricus fungus.

Further characteristically, the liquid culture medium used in the inventive method is admixed with a water-insoluble growth-supporting material selected from the group consisting of crushed sugarcane, sugarcane bagasse and wheat bran as well as crushed pine tree tissues including woody parts, leaves and fruits in an amount in the range from 0.2 to 15 g/liter calculated as dried material. The growth-supporting material added to the culture medium should be in the form of fine particles of fineness passing a screen of 100 mesh or, preferably, 200 mesh fineness in the Tyler standard. The particles of these growth-supporting materials serve as a core on which the fungus body aggregates grow with improved stability.

The inventors of course have conducted extensive screening tests for uncovering other growth-supporting materials derived from various plants including stalks and leaves of Indian corns, rice bran, barley grains and leaves and other parts of mulberry trees each in the form of fine particles to reach a conclusion that the growth-promoting and —stabilizing effect is specific to crushed sugarcane, sugarcane bagasse, wheat bran and pine tree tissues.

In conducting the inventive method for culturing a basidiomycetous fungus such as Agaricus fungus in the above described liquid culture medium, the first step is to inoculate the liquid culture medium containing the above described various ingredients with the fungus body which is preferably the mycelium of the fungus.

The most unexpected discovery leading to the present invention is that growth of the Agaricus fungus is greatly promoted with stability by conducting the culturing process under an oxygen-enriched condition which can be accomplished by blowing, into the above described liquid culture medium, oxygen-enriched air under pressurization so as to obtain a dissolved oxygen concentration of at least 7 mg $O_2$ per liter of the liquid culture medium. In order to accomplish this concentration of the dissolved oxygen, the oxygen-enriched air blown into the liquid medium contains at least 30% by volume of oxygen or, preferably, from 30 to 90% by volume of oxygen and the oxygen-enriched air is pressurized to have a pressure in the range from 0.12 to 0.5 MPa (absolute). The blowing rate of the oxygen-enriched air is of course of some importance and should be at least 0.01 liter/minute per liter of the liquid culture medium. The blowing rate has no particular upper limit but the blowing rate is preferably in the-range from 0.01 to 1.0 liter/minute per liter of the liquid medium in consideration of the increase in the mist dissipation carried off by the exhaust out of the gas outlet tube of the bioreactor. Needless to say, the oxygen-enriched air blown into the liquid culture medium must be sterilized, for example, by passing a suitable filter in order to minimize the risk of contamination of the liquid culture medium with various microorganisms which might be inhibitive against stable growth of the desired basidiomycetous fungus.

The temperature at which the culturing process of the Agaricus fungus is carried out is of course very important in order to obtain a best result of culturing. The temperature should be in the range from 20 to 30 ° C. for the basidiomycetous fungi in general and must be selected within this range depending on the particular species of the fungus under culturing for the optimum temperature. When the temperature is too low or too high, the growth rate of the fungus is disadvantageously decreased. When the requirements for the above described various factors are satisfied, the culturing process of the Agaricus fungus in a batch process is completed within 2 to 3 days.

It should be noted here that, as a consequence of the rapid growth of the fungus, a large volume of carbon dioxide gas is produced by the assimilation of the carbon source nutrient by the fungus body. Unless the carbon dioxide in the gaseous phase is adequately removed, growth of the fungus body is inhibited due to a decrease in the pH value of the liquid culture medium sometimes down to 3.5 or even lower as a result of the acidic external secretion from the fungus mycelia along with a decrease in the dissolved oxygen concentration therein by the decrease in the oxygen partial pressure in the gaseous phase above the liquid medium.

In the following, the culturing process of the invention and a bioreactor used therefor are illustrated by making reference to the accompanying drawing.

FIG. 1 schematically illustrates a bioreactor system including a culturing vessel consisting of a pressurizable cylindrical body 1 having a gas inlet tube 5 with a gas diffuser 5A at the lower part of the vessel 1, a gas outlet tube 6 connected to the upper part of the vessel 1 and a stirrer 7 with paddle blades to gently agitate the liquid culture medium 2 as driven by the motor M at the top. Oxygen-enriched air is blown into the liquid culture medium 2 through the gas inlet tube 5 as pressurized by a compressor 3 and sterilized by passing a sterilizing filter 4 under a specified pressure regulated by means of the pressure controller 8. The pressure of the gaseous phase over the liquid culture medium 2 in the vessel 1 is monitored and controlled by means of a constant-pressure valve under control of the exhaust pressure regulator 6A connected to the gas outlet tube 6. It is optional that a part of the exhaust air is returned to the air-feed pipeline to be mixed with the fresh air feed.

Figure 2:
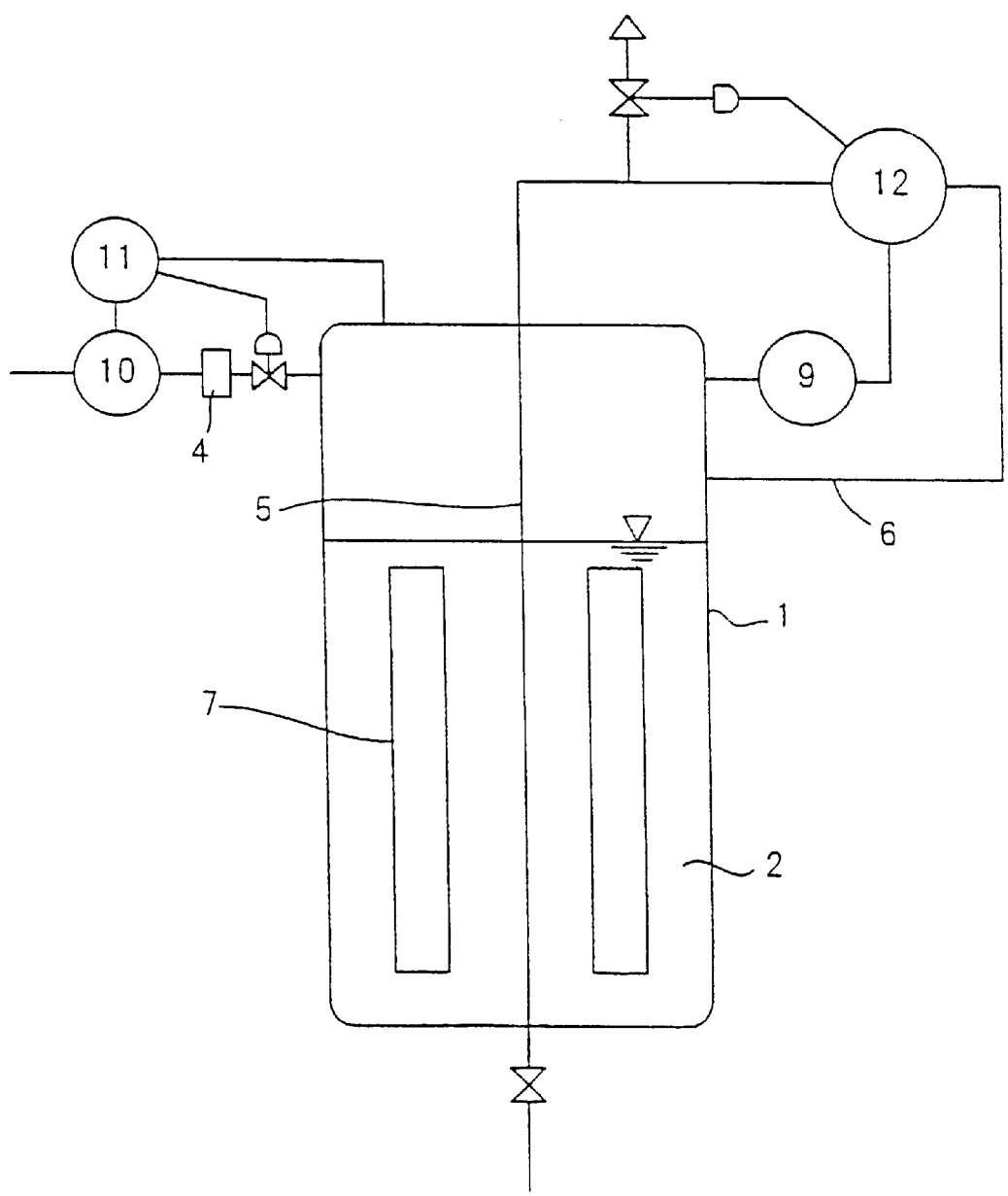
FIG. 2 is a schematic cross sectional view of another bioreactor system for practicing the method of the invention.

FIG. 2 is a schematic illustration of another bioreactor system to practice the inventive method, which is equipped with a carbon dioxide concentration controller 9 to discharge excess of carbon dioxide by means of a blower 12 and an oxygen modifier 10 combined with an oxygen concentration controller 11. The oxygen-enriched air inside of the vessel 1 over the liquid culture medium 2 discharged through the gas outlet tube 6 is circulated to the gas inlet tube 5 through the blower 12 along with removal of a part of carbon dioxide gas in the controller 9.

Figure 3:
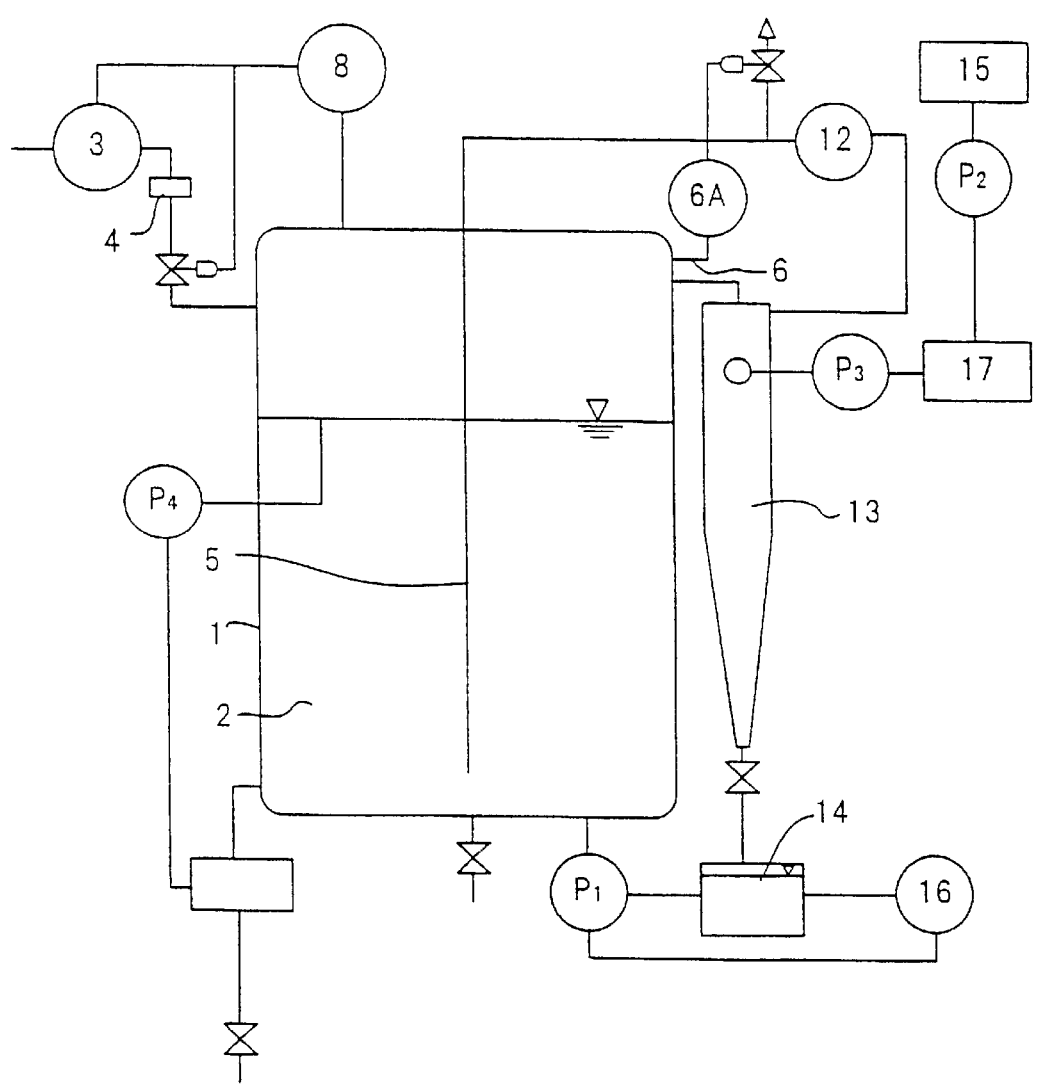
FIG. 3 is a schematic cross sectional view of a further different bioreactor system for practicing the method of the invention.

FIG. 3 is a schematic illustration of a further different bioreactor system for practicing the inventive method. When a basidiomycetous fungus is cultured in a culturing system by inoculating the liquid culture medium 2 with mycelia of the fungus, it is sometimes the case that the mist of the liquid culture medium 2 produced by blowing of oxygen-enriched air and containing the mycelia of the fungus under culturing is carried off by the exhaust air to cause deposition of the mycelia onto various parts of the system including the sterilizing filter 4, air discharge valves, inner wall of the pipelines and so on resulting in clogging of these parts so that the culturing run must be interrupted. In order to avoid such troubles, the bioreactor system is provided with a wet cyclone 13 and the mycelia separated in the cyclone 13 and deposited within the cyclone 13 are washed down in the conical part of the cyclone 13 with the liquid sent thereto. The liquid washing containing the mycelia thus washed down is discharged out of the bottom of the cyclone 13 and received in the receiver tank 14 connected to the bottom of the cyclone 13, from which the liquid is returned, to the reactor vessel 1 by means of the pump $P_1$ under a pressure controlled by means of the pressure controller 16. When adequately designed and operated, the culturing process of a basidiomycetous fungus can be continued without interruption for 4 days or even longer.

Figure 4:
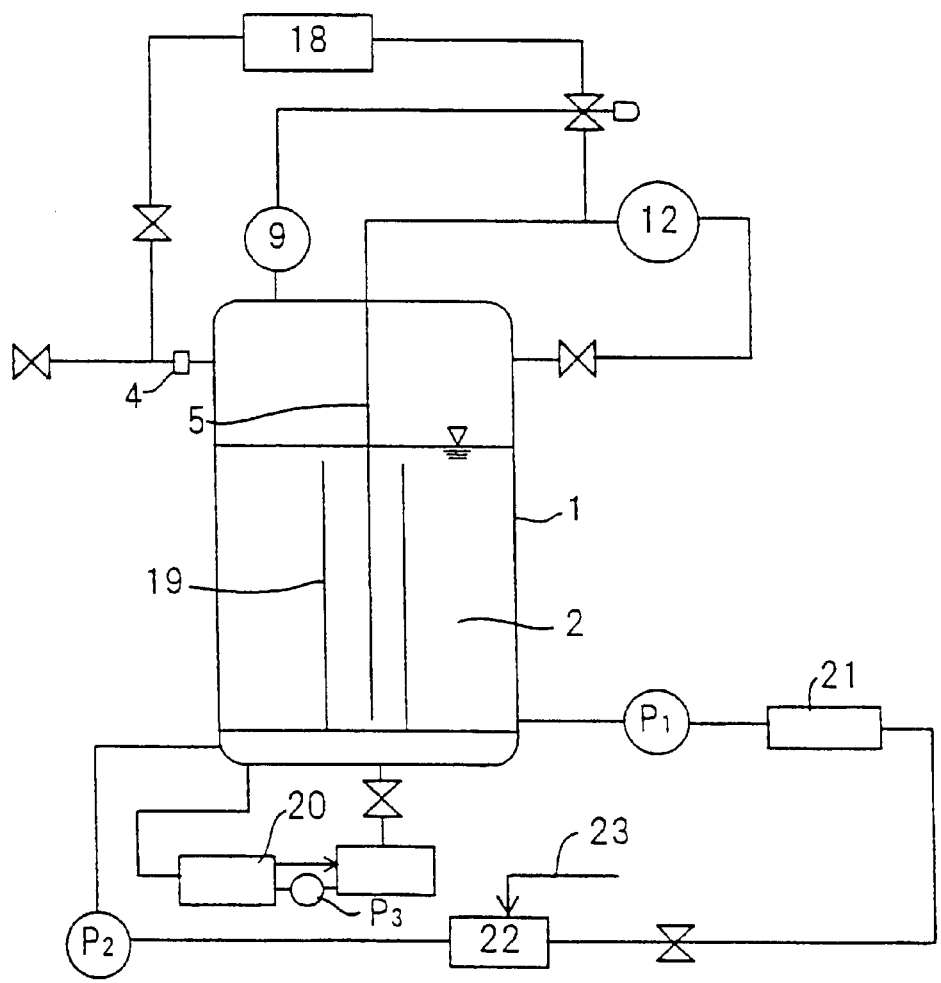
FIG. 4 is a schematic cross sectional view of a bioreactor system for practicing the method of the invention as a continuous process.

FIG. 4 is a schematic illustration of a bioreactor system suitable for practicing the method of the invention as a continuous process, in which the carbon dioxide gas produced by culturing of the fungus is removed by operating the carbon dioxide absorber 18 and the air having a decreased concentration of carbon dioxide is returned to the culture system through a carbon dioxide concentration controller 9. The air inlet tube 5 is surrounded by a jacket tube 19 which enables upward flowing of the liquid medium within the jacket tube so as to enhance the growth rate of the fungus aggregates even in the absence of a mechanical agitating means such as a stirrer. The liquid culture medium 2, which is prepared in the preparation tank 22 with supplemental addition of the nutrient ingredients through the pipe line 23, is circulated through microfilters or ultrafiltration membranes 20, 21 to remove the suspended fungus mycelia.

In the following, the method of the present invention is described in more detail by way of Examples in which the Agaricus fungus was taken as a typical species of the basidiomycetous fungi.

EXAMPLE 1

A pressurizable cylindrical stainless steel bioreactor vessel of 1 liter capacity was charged with 1 liter of a liquid culture medium containing 60 g of pure sucrose, 10 g of ammonium nitrate, 5 g of sodium phosphate, 2.5 g of magnesium sulfate heptahydrate $MgSO_4.7H_2O$, 5 g of dipotassium hydrogenphosphate $K_2HPO_4$ and 0.2 g of iron (II) sulfate heptahydrate $FeSO_4.7H_2O$ each per liter of the liquid medium.

The thus prepared liquid culture medium was inoculated with 3 mg as dry of the mycelia of the Agaricus fungus contaminated with actinomyces and gently agitated at 25° C. for 3 days to obtain 25 g as dry of granules of the fungus body.

Two fungus granules free from coloration inherent in true bacteria by visual inspection were picked up from the thus obtained mass of granules and triturated in a clean bench. A 1 liter volume of another liquid culture medium containing 60 g of crude cane sugar corresponding to 58 g of sucrose, 10 g of a dried powder of crushed sugarcane having a particle fineness to pass a 200 mesh screen, 12 g of ammonium nitrate, 4 g of sodium phosphate, 2.5 g of magnesium sulfate heptahydrate, 0.2 g of iron (II) sulfate heptahydrate and 5 g of dipotassium hydrogenphosphate dissolved or dispersed each per liter of the liquid medium was inoculated with the triturated fungus granules and culturing was conducted in a batch process. After repeating again this batch process culturing under the same conditions, the fungus mycelia were cultured on a conventional nutrient agar culture medium to obtain fungus body granules free from contamination.

Similar uncontaminated Agaricus granules could be obtained by conducting culturing in the same liquid culture medium inoculated with the initial granules contaminated with actinomyces from which the colored portions contaminated with actinomyces had been shaved off by using a knife.

EXAMPLE 2

A pressurizable stainless steel bioreactor vessel connected to a cyclone as illustrated in FIG. 3 of 1 liter capacity was charged with 1 liter volume of a first liquid culture medium, referred to as the culture medium A hereinafter, containing 60 g of purified sucrose, 10 g of ammonium nitrate, 5 g of sodium phosphate, 2.5 g of magnesium sulfate heptahydrate, 0.2 g of iron (II) sulfate heptahydrate and 7 g of dipotassium hydrogenphosphate dissolved therein each per liter of the liquid medium.

A further pressurizable stainless steel bioreactor vessel of 1 liter capacity was charged with 1 liter of a second liquid culture medium, referred to as the culture medium. B hereinafter, containing 50 g of crude cane sugar, 15 g as dried of a sugarcane bagasse powder having a particle fineness to pass a 200 mesh screen, 12 g of ammonium nitrate, 4 g of sodium phosphate, 2.5 g of magnesium sulfate heptahydrate, 0.2 g of iron (II) sulfate heptahydrate and 6 g of dipotassium hydrogenphosphate dissolved or dispersed therein each per liter of the liquid medium.

Each of the cultured media A and B was inoculated with the uncontaminated Agaricus fungus granules obtained in Example 1 and culturing of the fungus was conducted at 25° C. under gentle agitation of the liquid medium while oxygen-enriched air containing 30 to 35% by volume of oxygen was blown into the liquid medium at a rate of 0.8 liter/minute. The pressure of the oxygen-enriched air blown into the liquid medium was controlled in such a way that the upstream-side pressure was kept at 0.12 to 0.15 MPa (absolute) for the first 24 hours and at 0.15 to 0.30 MPa (absolute) for the second to fourth days while the downstream-side pressure was kept always at 0.10 to 0.13 MPa (absolute).

Figure 5:
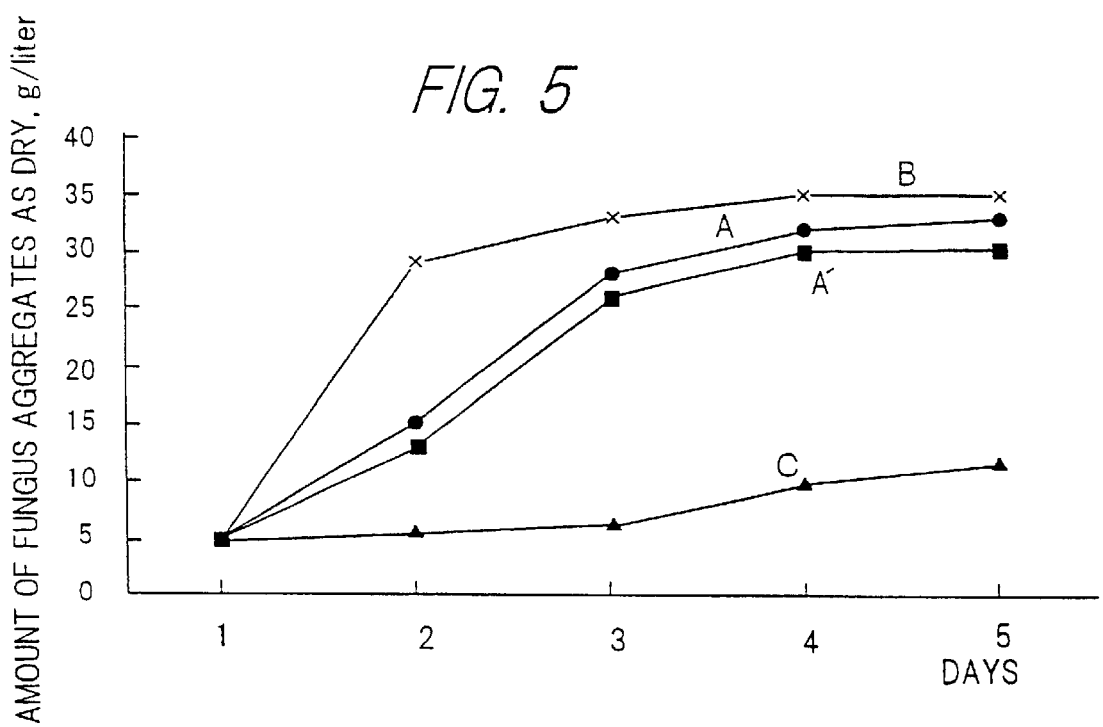
FIG. 5 shows growth curves of Agaricus fungus in various liquid culture media.

The amounts of the fungus aggregates (dry basis) thus obtained by culturing for up to 5 days are shown by the curves A and B in FIG. 5 for the liquid culture media (A) and (B), respectively. The curve A' in FIG. 5 shows the results obtained in the liquid culture medium (A) without agitation with the stirrer driven. The curve C in FIG. 5 shows the results obtained in culturing in a conventional liquid culture medium which was the same as the liquid culture medium (A) excepting for the replacement of sucrose with the same amount of glucose.

EXAMPLE 3

The same culturing process of the Agaricus fungus as in Example 2 was repeated by using the liquid culture medium (B). After 24 hours of running, the liquid surface was covered with a substantial volume of foams which were skimmed up and reserved. Another run of Agaricus culturing was undertaken in the same manner as in Example 2 with a fresh portion of the liquid culture medium (B) and, after 3 hours of running, the liquid culture medium was admixed with the foams reserved above in a volume of about 10% of the liquid medium to continue further running of culturing up to 5 days.

The results of culturing obtained in this run were substantially the same as those shown by the curve B in FIG. 5 indicating that the foams could exhibit antimicrobial-activity against eubacteria and eumycetes.

EXAMPLE 4

Figure 6:
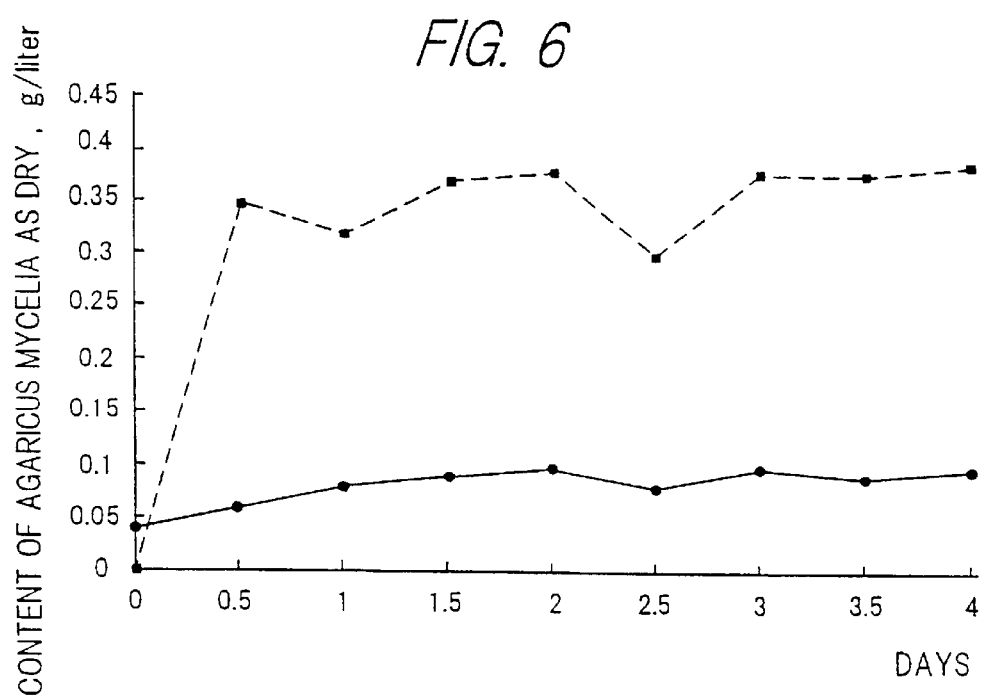
FIG. 6 shows the mycelium concentration of Agaricus fungus in the mist carried off from a bioreactor equipped (solid-line curve) or not equipped (broken-line curve) with a gas cyclone.

The same culturing procedure of the Agaricus fungus was conducted over 4 days in the same manner as in Example 1 in a bioreactor with a cyclone as is illustrated in FIG. 3 or in the same reactor excepting for omission of the cyclone. The liquid discharged from the bioreactor as being carried by the exhaust air was analyzed for the content of the Agaricus mycelia getting out as accompanying the mist to give the results shown in FIG. 6 by the solid line curve and the broken line curve for the runs with and without the cyclone, respectively. As is indicated in this figure, the content of the Agaricus mycelia in the mist could be kept not to exceed 0.1 g as dry per liter of the liquid when the cyclone was equipped while the mycelia content reached 0.4 g as dry per liter of the liquid when no cyclone was equipped.

What is claimed is:

1. A method for culturing a basidiomycetous fungus in an aqueous liquid culture medium which comprises the steps of:

(a) inoculating a liquid culture medium containing inorganic nutrient salts for nitrogen, phosphate and potassium with a body of the fungus;

(b) admixing the liquid culture medium with crude cane sugar in an amount in the range from 50 g to 70 g calculated as sucrose per liter of the liquid culture medium;

(c) admixing the liquid culture medium with a water-insoluble growth-supporting material selected from the group consisting of crushed sugarcane, sugarcane bagasse, pine tree-tissue and wheat bran in an amount in the range from 0.2 g to 15 g as dry per liter of the liquid culture medium;

(d) keeping the liquid culture medium under agitation at a temperature in the range from 20 to 30 ° C.; and (e) blowing, into the liquid culture medium, oxygen-enriched air containing at least 30% by volume of oxygen under a pressure in the range from 0.12 to 0.5 MPa (absolute) at a rate of at least 0.01 liter/minute per liter of the liquid culture medium.

2. The method for culturing a basidiomycetous fungus in an aqueous liquid culture medium according to claim 1 in which the water-insoluble growth-supporting material added to the liquid culture medium in step (c) is in the form of a powder having a particle size to pass a 100 mesh screen.

3. The method for culturing a basidiomycetous fungus in an aqueous liquid culture medium according to claim 2 in which the water-insoluble growth-supporting material added to the liquid culture medium in step (c) is in the form of a powder having a particle size to pass a 200 mesh screen.

4. The method for culturing a basidiomycetous fungus in an aqueous liquid culture medium according to claim 1 in which the oxygen-enriched air blown into the liquid culture medium in step (e) contains from 30% to 90% by volume of oxygen.

5. The method for culturing a basidiomycetous fungus in an aqueous liquid culture medium according to claim 1 in which the blowing rate of the oxygen-enriched air into the liquid culture medium in step (e) is in the range from 0.01 to 1.0 liter/minute per liter of the liquid culture medium.

6. The method for culturing a basidiomycetous fungus in an aqueous liquid culture medium according to claim 1 which further comprises the step of:

(f) controlling the concentration of carbon dioxide in the gaseous phase over the liquid culture medium.

* * * * *

UNITED STATES PATENT AND TRADEMARK OFFICE
CERTIFICATE OF CORRECTION

PATENT NO.     : 6,490,824 B1                                              Page 1 of 1
DATED          : December 10, 2002
INVENTOR(S)    : Takaaki Maekawa It is certified that error appears in the above-identified patent and that said Letters Patent is hereby corrected as shown below:

<u>Title page,</u>
Item [73], please change the spelling of the Assignee from "Tsukuba Biosystems, Ltd." to -- Tsukuba Biosystem, Ltd. --.

Signed and Sealed this

Twenty-second Day of July, 2003

JAMES E. ROGAN
*Director of the United States Patent and Trademark Office*